United States Patent
Isogai et al.

(10) Patent No.: US 12,396,899 B2
(45) Date of Patent: Aug. 26, 2025

(54) ABSORBENT PRODUCT PROVIDED WITH FECES INDICATOR AND URINE INDICATOR

(71) Applicant: UNICHARM CORPORATION, Ehime (JP)

(72) Inventors: Tomomi Isogai, Kagawa (JP); Shota Uto, Kagawa (JP); Takuya Miyama, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 800 days.

(21) Appl. No.: 17/697,190

(22) Filed: Mar. 17, 2022

(65) Prior Publication Data

US 2022/0202628 A1 Jun. 30, 2022

Related U.S. Application Data

(63) Continuation of application No. PCT/JP2020/033080, filed on Sep. 1, 2020.

(30) Foreign Application Priority Data

Nov. 1, 2019 (JP) .................. 2019-200034

(51) Int. Cl.
*A61F 13/42* (2006.01)
*A61F 13/84* (2006.01)

(52) U.S. Cl.
CPC ........ *A61F 13/42* (2013.01); *A61F 2013/422* (2013.01); *A61F 2013/8497* (2013.01)

(58) Field of Classification Search
CPC .. A61F 13/42; A61F 13/514; A61F 13/51478; A61F 13/51484
See application file for complete search history.

(56) References Cited

U.S. PATENT DOCUMENTS

| 5,078,708 A * | 1/1992 | Haque | A61F 13/42 604/361 |
| 6,710,221 B1 * | 3/2004 | Pierce | A61F 13/42 604/361 |

(Continued)

FOREIGN PATENT DOCUMENTS

| CN | 102573713 A | 7/2012 |
| CN | 103052371 A | 4/2013 |

(Continued)

OTHER PUBLICATIONS

Pohlmann, A. Measures and numbers for colors. The color system of Wilhelm Ostwald. ChemTexts 6, 9 (2020). https://doi.org/10.1007/s40828-020-0104-5.*

(Continued)

*Primary Examiner* — Michele Kidwell
(74) *Attorney, Agent, or Firm* — Osha Bergman Watanabe & Burton LLP

(57) ABSTRACT

An absorbent article includes: a liquid absorbent body; a feces indicator that visually changes between two colors, the feces indicator changing, on contact with feces, from a pre-feces-contact color to a post-feces-contact color; and a urine indicator that visually changes between two colors, the urine indicator changing, on contact with urine, from a pre-urine-contact color to a post-urine-contact color, the feces indicator and the urine indicator being disposed on a non-skin side in a thickness direction with respect to the absorbent body, and one of the two colors of the feces indicator being visually similar to one of the two colors of the urine indicator, whereas the other of the two colors of the feces indicator being visually dissimilar to the other of the two colors of the urine indicator.

12 Claims, 8 Drawing Sheets

(56) References Cited

U.S. PATENT DOCUMENTS

| | | | | |
|---|---|---|---|---|
| 2008/0208151 A1* | 8/2008 | Zacharias | ............... | A61F 13/42 604/361 |
| 2008/0228157 A1* | 9/2008 | McKiernan | ............ | A61F 13/42 604/361 |
| 2010/0168699 A1* | 7/2010 | Robles | .................... | A61F 13/42 604/385.01 |
| 2010/0168700 A1* | 7/2010 | Schmidt | .................. | A61F 13/42 604/385.01 |
| 2014/0378922 A1* | 12/2014 | Fuchs | .................... | A61F 13/42 604/361 |
| 2017/0165123 A1* | 6/2017 | Gogin | .................... | A61L 15/56 |
| 2017/0290713 A1* | 10/2017 | LaVon | .................... | A61F 13/42 |
| 2019/0336353 A1* | 11/2019 | Arizti | .................... | A61B 5/6808 |
| 2020/0107971 A1* | 4/2020 | Onishi | ............. | A61F 13/51496 |
| 2022/0202627 A1* | 6/2022 | Uto | .................. | A61F 13/49001 |

FOREIGN PATENT DOCUMENTS

| | | | | |
|---|---|---|---|---|
| CN | 104582653 A | 4/2015 | | |
| CN | 105392456 A | 3/2016 | | |
| CN | 107049611 A | 8/2017 | | |
| JP | 2004337385 | * 12/2004 | ............. | A61F 13/42 |
| JP | 2007268221 A | 10/2007 | | |
| JP | 2012100886 A | 5/2012 | | |
| JP | 2020081340 A | 6/2020 | | |
| WO | 2013/187742 A1 | 12/2013 | | |
| WO | 2015194973 A1 | 12/2015 | | |

OTHER PUBLICATIONS

International Preliminary Report on Patentability issued in corresponding International Application No. PCT/JP2020/033080; dated May 3, 2022 (5 pages).

International Search Report issued in corresponding International Application No. PCT/JP2020/033080 mailed Nov. 24, 2020 (9 pages).

Written Opinion issued in corresponding International Application No. PCT/JP2020/033080 mailed Nov. 24, 2020 (4 pages).

Office Action issued in the counterpart Chinese Patent Application No. 202080074836.X, mailed Jul. 13, 2022 (6 pages), (no translation provided).

* cited by examiner

ABSORBENT PRODUCT PROVIDED WITH FECES INDICATOR AND URINE INDICATOR

BACKGROUND

Technical Field

The present invention relates to an absorbent article.

Description of Related Art

As an example of absorbent articles, a disposable diaper is given. Some of such disposable diapers have an indicator function of visualizing the amount of excrement absorbed and informing the user of the time for replacement. For example, Patent Literature 1 discloses a disposable diaper including a urination indicator whose color changes when coming into contact with urine, between an absorbent body and a back-surface sheet of the disposable diaper. In that disposable diaper, the visibility of the indicator is enhanced by compressing an outer-layer nonwoven fabric in a portion that overlaps the indicator.

Patent Literature 1: Japanese Patent Application Publication No. 2012-100886

According to the disposable diaper of Patent Literature 1, a person replacing the diaper can visually recognize from the outside of the diaper that urination has occurred. However, in the case where the absorbent article includes not only the urine indicator but also a feces indicator whose color is changed due to (on) contact with feces, there is a risk that it may be it makes a person replacing the absorbent article difficult to remember the color tones of the urine indicator and the feces indicator before and after the reaction of the urine indicator and the feces indicator.

SUMMARY

One or more embodiments of the present invention provide an absorbent article which allows a person replacing the absorbent article to recognize that urination and/or defecation have occurred, even when the replacing person neither remember the actual pre-use colors of the urine indicator and the feces indicator nor the colors to which the urine indicator and the feces indicator will change.

An aspect of the present invention is an absorbent article having a longitudinal direction, a width direction, and a thickness direction in an unfolded state, the absorbent article including: a liquid-absorbent absorbent body (or liquid absorbent body); a feces indicator that visually changes a color due to contact with feces (i.e., visually changes between two colors, the feces indicator changing, on contact with feces, from a pre-feces-contact color to a post-feces-contact color); and a urine indicator that visually changes a color due to contact with urine (i.e., visually changes between two colors, the urine indicator changing, on contact with urine, from a pre-urine-contact color to a post-urine-contact color), the feces indicator and the urine indicator being located on a non-skin side in the thickness direction with respect to the absorbent body, the feces indicator having a pre-change color that is a color before the color of the feces indicator is changed and a post-change color that is a color after the color of the feces indicator is changed, the urine indicator having a pre-change color that is a color before the color of the urine indicator is changed and a post-change color that is a color after the color of the urine indicator is changed, concerning either one color of the pre-change color and the post-change color of the feces indicator, concerning either one color of the pre-change color and the post-change color of the urine indicator, the either one color of the feces indicator and the either one color of the urine indicator being similar (or analogous) colors, concerning another color of the pre-change color and the post-change color of the feces indicator, concerning another color of the pre-change color and the post-change color of the urine indicator, the other color of the feces indicator and the other color of the urine indicator being dissimilar colors (i.e., one of the two colors of the feces indicator is visually similar to one of the two colors of the urine indicator, whereas the other of the two colors of the feces indicator is visually dissimilar to the other of the two colors of the urine indicator), when the pre-change color and the post-change color of each of the feces indicator and the urine indicator (i.e., the pre-feces-contact color, the pre-urine-contact color, the post-feces-contact color, and the post-urine-contact color) are specified as closest hues among 24 color hues of an Ostwald color wheel, a degree of the similar colors being that the similar colors have an identical hue in the Ostwald color wheel, or that the similar colors are in a range in which a difference between color numbers of the similar colors is less than 6 (i.e., a similarity degree between the one of the two colors of the feces indicator and the one of the two colors of the urine indicator is either one of: having an identical hue in the Ostwald color wheel, and being within a range in which a difference between color numbers is less than 6 in the Ostwald color wheel), a degree of the dissimilar colors being that the color numbers of the dissimilar colors in the Ostwald color wheel are apart by 6 or more from each other (i.e., a dissimilarity degree between the other of the two colors of the feces indicator and the other of the two colors of the urine indicator is having color numbers that are apart by 6 or more from each other in the Ostwald color wheel).

Features of one or more embodiments of the present invention other than the above will become clear by reading the description of the present specification with reference to the accompanying drawings.

According to one or more embodiments of the present invention, it is possible to provide an absorbent article which allows a person replacing the absorbent article to recognize that urination and/or defecation have occurred, even when the replacing person neither remember the actual pre-use colors of the urine indicator and the feces indicator nor the colors to which the urine indicator and the feces indicator will change.

DETAILED DESCRIPTION OF EMBODIMENTS

Figure 1:
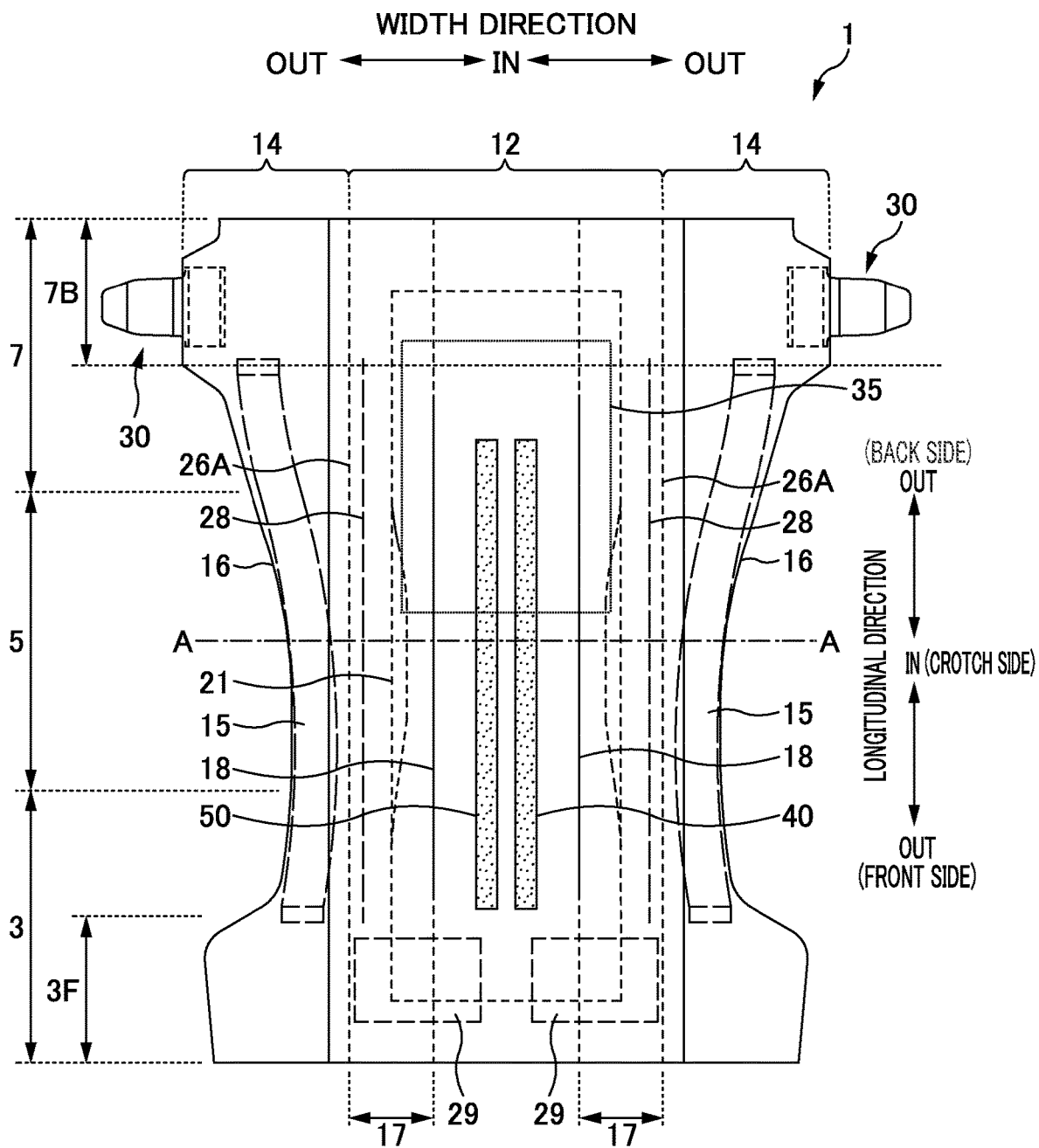
FIG. 1 is a plan view of a tape-type disposable diaper 1 in an unfolded and stretched state.

At least following matters will become clear with description of this specification and attached drawings.

an absorbent article having a longitudinal direction, a width direction, and a thickness direction in an unfolded state, the absorbent article including: a liquid-absorbent absorbent body; a feces indicator that visually changes a color due to contact with feces; and a urine indicator that visually changes a color due to contact with urine, the feces indicator and the urine indicator being located on a non-skin side in the thickness direction with respect to the absorbent body, the feces indicator having a pre-change color that is a color before the color of the feces indicator is changed and a post-change color that is a color after the color of the feces indicator is changed, the urine indicator having a pre-change color that is a color before the color of the urine indicator is changed and a post-change color that is a color after the color of the urine indicator is changed, concerning either one color of the pre-change color and the post-change color of the feces indicator, concerning either one color of the pre-change color and the post-change color of the urine indicator, the either one color of the feces indicator and the either one color of the urine indicator being similar colors, concerning another color of the pre-change color and the post-change color of the feces indicator, concerning another color of the pre-change color and the post-change color of the urine indicator, the other color of the feces indicator and the other color of the urine indicator being Dissimilar colors, when the pre-change color and the post-change color of each of the feces indicator and the urine indicator are specified as closest hues among 24 color hues of an Ostwald color wheel, a degree of the similar colors being that the similar colors have an identical hue in the Ostwald color wheel, or that the similar colors are in a range in which a difference between color numbers of the similar colors is less than 6, a degree of the dissimilar colors being that the color numbers of the dissimilar colors in the Ostwald color wheel are apart by 6 or more from each other.

According to the absorbent article, a color change occurs in each of the feces indicator and the urine indicator after the reaction. By setting the colors of both indicators to the similar colors before or after the reaction, it is possible for a person replacing the absorbent article to recognize that defecation, urination, or both have occurred even when the replacing person does not remember the actual colors of the indicators (or what colors will the colors of the indicators change to). For example, when the indicators having the similar colors no longer have the similar colors, it triggers that the replacing person can recognize the occurrence of the color change and can recognize that at least defecation or urination has occurred. Conversely, when the indicators not having similar colors become the similar colors, it triggers that the replacing person can recognize the occurrence of the color change and can recognize that at least defecation or urination has occurred. Further, by setting to the dissimilar colors the colors before becoming the similar colors or the colors after having changed from the similar colors, it is possible to avoid that the colors change from the similar color to the similar color. This makes it possible for the replacing person to recognize the color change without confusion.

In such an absorbent article, the pre-change color of the feces indicator and the pre-change color of the urine indicator may be the similar colors.

According to the absorbent article, the colors (pre-change colors) of the feces indicator and the urine indicator before the reaction are the similar colors, and therefore in the case where defecation and/or urination have occurred, the color tones of the two indicators having the similar colors are changed and are no longer the similar colors. Accordingly, even when the person replacing the absorbent article does not remember the pre-change colors, the fact that the colors of the two indicators are no longer the similar colors makes it possible for the replacing person to recognize the occurrence of the color change. This makes it possible to recognize at least that defecation or urination has occurred.

In such an absorbent article, the post-change color of the feces indicator and the post-change color of the urine indicator may be the similar colors.

According to the absorbent article, the color tones (pre-change colors) of the feces indicator and the urine indicator before use of the absorbent article are different colors from each other. And the color tones (post-change colors) of the indicators are set to become the similar colors at the time when urination and defecation both have occurred. Even when the person replacing the absorbent article does not remember the colors which is before the reaction or even when the replacing person does not recognize what colors will the colors of the indicators change to after the reaction, the colors of both indicators becoming the similar colors makes it possible to recognize that defecation or urination has occurred.

In such an absorbent article, the post-change color of the feces indicator and the pre-change color of the urine indicator may be the similar colors.

According to the absorbent article, the color tones (pre-change colors) of the feces indicator and the urine indicator before use of the absorbent article are different colors from each other. However, in the case where only defecation has occurred, the color (post-change color) of the feces indicator and the color (pre-change color) of the urine indicator become the similar colors. Even when the replacing person does not remember the color tone of the feces indicator before defecation, by changing to similar colors the colors of both indicators which do not have the similar colors, it is possible for the replacing person to recognize the occurrence of the color change and to recognize that defecation has occurred.

In such an absorbent article, the pre-change color of the feces indicator and the post-change color of the urine indicator may be the similar colors.

According to the absorbent article, the color tones (pre-change colors) of the feces indicator and the urine indicator before use of the absorbent article are different colors from each other. However, in the case where only urination has occurred, the color (post-change color) of the urine indicator and the color (pre-change color) of the feces indicator become the similar colors. Even when the replacing person does not remember the color tone of the urine indicator before urination, by changing to similar colors the colors of both indicators which do not have the similar colors, it is possible for the replacing person to recognize the occurrence of the color change and to recognize that urination has occurred.

In such an absorbent article, the pre-change color and the post-change color of the feces indicator may be dissimilar colors.

According to the absorbent article, the pre-change color and the post-change color being the dissimilar colors makes clear the difference in color before and after the reaction. This makes the person replacing the absorbent article easier to visually recognize that defecation has occurred.

In such an absorbent article, the absorbent article may further comprise a back sheet that is located on the non-skin side in the thickness direction with respect to the feces indicator and the urine indicator, the back sheet may have a graphic, the either one color of the feces indicator, the either one color of the urine indicator, and a color tone of the graphic may be the similar colors, and the graphic may overlap at least either of the feces indicator and the urine indicator when viewed in the thickness direction.

According to the absorbent article, making three of the urine indicator, the feces indicator, and the graphic on the back sheet have the similar colors makes the person replacing the absorbent article easier to notice the similarity of the colors. In other words, in the case where the three items, namely the urine indicator, the feces indicator, and the graphic, have the similar colors before use, only changing at least the color of the urine indicator or the feces indicator makes it easier to notice the color change. This makes it possible to recognize that at least urination or defecation has occurred. Even in the case where the color tones of the three items all become the similar colors after the reaction, all of the color tones becoming the similar colors makes it easier to notice the change. This makes it easier to recognize that urination and defecation have occurred.

In such an absorbent article, the absorbent article may further comprise: a back sheet that is located on the non-skin side in the thickness direction with respect to the feces indicator and the urine indicator; and an exterior sheet that forms an exterior of the absorbent article, the back sheet may have a light transmittance of 30% to 80%, and the exterior sheet may have a light transmittance of 50% or more.

According to the absorbent article, the back sheet and the exterior sheet having high light transmittances makes it easier to visually recognize the feces indicator and the urine indicator through from the outside of the absorbent article. This makes the person replacing the absorbent article easier to recognize the degree of color change.

In such an absorbent article, the feces indicator may be arranged so as to straddle a longitudinal central portion of the absorbent article.

According to the absorbent article, the longitudinal central portion of the absorbent article is a position where the absorbent article is folded one time, and the front side and the back side of the absorbent article are distinguished with reference to the position. Arranging the feces indicator so as to cover both of the front side and the back side of the absorbent article in the longitudinal direction makes it easier to detect feces in the case of defecation which is made not only when the user is in a lying-down state but also when the user is in a standing state or the like.

In such an absorbent article, the absorbent article may further comprise: a front waist portion that is positioned on (or fit to) a wearer's front waist during usage of the absorbent article; and a back waist portion that is positioned on (or fit to) a wearer's back waist during usage of the absorbent article, and the feces indicator may overlap the back waist portion when viewed in the thickness direction.

According to the absorbent article, since feces have low moisture unlike urine, it is advantageous to arrange the feces indicator close to the back-side in order for the feces indicator to react with the low moisture. In addition, arranging the feces indicator to extend to the upper side of the back-side, that is, to extend to the further outside in the longitudinal direction increases a possibility that the uppermost end (outer end) of the feces indicator does not react with the feces and the pre-change color remains. The feces indicator having the two-color structure composed of the pre-change color portion and the post-change color portion makes it easier to recognize that a change has occurred.

In such an absorbent article, among the 24 color hues of the Ostwald color wheel, when hues that are respectively closest to the pre-change color and the post-change color of the urine indicator are specified, letting the hue specified as the pre-change color of the urine indicator be a first hue, letting the hue specified as the post-change color of the urine indicator be a second hue, and when hues that are respectively closest to the pre-change color and the post-change color of the feces indicator are specified, letting the hue specified as the pre-change color of the feces indicator be a third hue, letting the hue specified as the post-change color of the feces indicator be a fourth hue, a difference in color number between the first hue and the second hue may be larger than a difference in color number between the third hue and the fourth hue.

According to the absorbent article, a large hue difference means a large color change, and a large color change makes it easier to recognize the change. That the color change of the urine indicator before and after the reaction is larger than the color change of the feces indicator before and after the reaction enables to more easily to recognize the occurrence of urination, making it possible to preferentially detect urine.

In such an absorbent article, among the 24 color hues of the Ostwald color wheel, when hues that are respectively closest to the pre-change color and the post-change color of the urine indicator are specified, letting the hue specified as the pre-change color of the urine indicator be a first hue, letting the hue specified as the post-change color of the urine indicator be a second hue, and when hues that are respectively closest to the pre-change color and the post-change color of the feces indicator are specified, letting the hue specified as the pre-change color of the feces indicator be a third hue, letting the hue specified as the post-change color of the feces indicator be a fourth hue, a difference in color number between the third hue and the fourth hue may be larger than a difference in color number between the first hue and the second hue.

According to the absorbent article, a large hue difference means a large color change, and a large color change makes it easier to recognize the change. That the color change of the feces indicator before and after the reaction is larger than the color change of the urine indicator before and after the reaction allows the person replacing the absorbent article to more easily recognize that defecation has occurred.

In such an absorbent article, among the 24 color hues of the Ostwald color wheel, when hues that are respectively closest to the pre-change color and the post-change color of the urine indicator are specified, letting the hue specified as the pre-change color of the urine indicator be a first hue, letting the hue specified as the post-change color of the urine indicator be a second hue, and when hues that are respectively closest to the pre-change color and the post-change color of the feces indicator are specified, letting the hue specified as the pre-change color of the feces indicator be a third hue, letting the hue specified as the post-change color of the feces indicator be a fourth hue, a difference in color number between the first hue and the second hue may be equal to a difference in color number between the third hue and the fourth hue.

According to the absorbent article, that the color changes of the urine indicator and the feces indicator are substantially the same makes it easier to recognize the changes of both indicators without making the change of only one of the indicators conspicuous.

The following describes an example of a tape-type disposable diaper for infants as an absorbent article according to one or more embodiments of the present invention. However, there is no limitation thereto. The present invention is also applicable to, for example, a pull-on disposable diaper, a pad-type disposable diaper, a tape-type disposable diaper for adults, and the like.

Basic Configuration of Tape-Type Disposable Diaper 1

Figure 2:
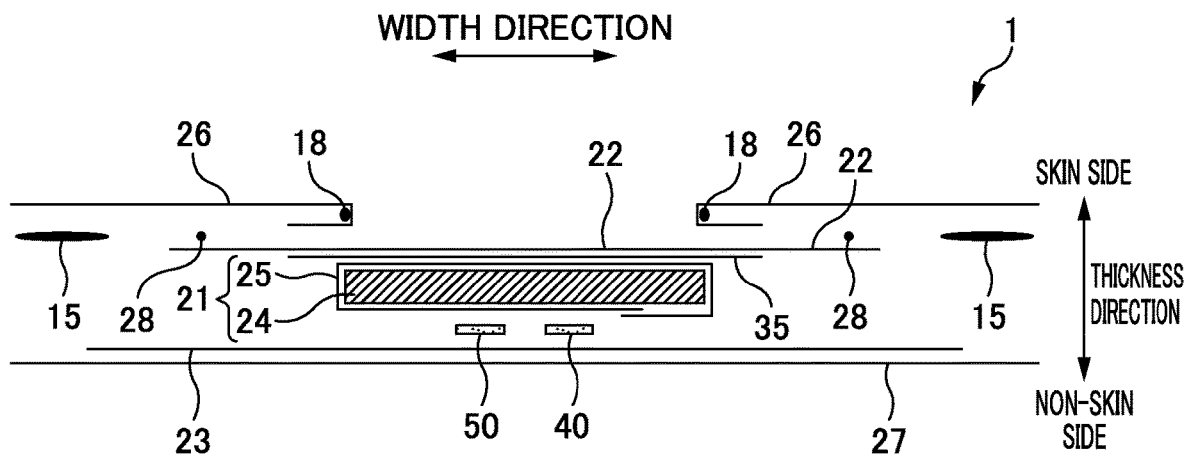
FIG. 2 is a cross-sectional view taken along a line A-A of FIG. 1.

FIG. 1 is a plan view of a tape-type disposable diaper 1 (hereinafter, also referred to as a "diaper 1") in an unfolded and stretched state. FIG. 2 is a cross-sectional view taken along a line A-A of FIG. 1. The unfolded state of the diaper 1 refers to a state in which the diaper 1 is unfolded on a plane by opening the diaper 1 in the longitudinal direction. In addition, the stretched state of the diaper 1 refers to a state where the diaper 1 has been unfolded and stretched such that wrinkles formed in the diaper 1 are substantially no longer visible, that is to say a state where the diaper 1 has been stretched until the dimensions of constituent members of the diaper 1 (e.g., a later-described top sheet 22) match or are close to the dimensions of the members on their own.

The diaper 1 of one or more embodiments is a so-called open-type disposable diaper and has a front portion 3, a crotch portion 5, and a back portion 7 in the longitudinal direction as shown in FIG. 1. The front portion 3 is a portion that is located at the wearer's front portion (front side) while the diaper 1 is put on. The back portion 7 is a portion that is located at the wearer's back portion (back side) while the diaper 1 is put on. The crotch portion 5 is provided between the front portion 3 and the back portion 7.

As shown in FIG. 1, the directions used in the following description are defined as follows. That is, in an unfolded state as viewed from above, the direction from the front portion 3 toward the back portion is defined as the "longitudinal direction" and the direction orthogonal to the longitudinal direction is defined as the "width direction". The line A-A shown in FIG. 1 indicates the center of the diaper 1 in the longitudinal direction. Further, as shown in FIG. 2, the direction orthogonal to the longitudinal direction and the width direction is defined as the "thickness direction", the side facing the wearer's skin is defined as the "skin side", and a side opposite to the skin side is defined as the "non-skin side".

The diaper 1 includes a central band-shaped region 12, side flaps 14, leg gathers 16, and leg side gathers 17. Fastening tapes 30 are respectively attached to the back portion 7 of the pair of side flaps 14.

The central band-shaped region 12 is a band-shaped region that is located in the central portion in the width direction and that is constituted by the front portion 3, the crotch portion 5, and the back portion 7 (see FIG. 1). The central band-shaped region 12 is a portion that absorbs and holds a liquid such as urine that is excreted by the wearer. The central band-shaped region 12 has a longitudinally-elongated shape (shape extending along the longitudinal direction) that includes a liquid-retaining absorbent body 21. The central band-shaped region 12 mainly includes: the absorbent body 21; a liquid-permeable top sheet 22 that covers the liquid-absorbent absorbent body 21 from the skin side; a liquid-impermeable back sheet 23 that covers the absorbent body 21 from the non-skin side; and an exterior sheet 27 that forms the exterior of the diaper 1 (e.g., a nonwoven fabric) (see FIG. 2). In the central band-shaped region 12, a liquid-permeable second sheet 35 is further provided. However, it is not necessarily required that the second sheet 35 is provided.

As shown in FIG. 2, the absorbent body 21 of one or more embodiments includes an absorbent core 24 that absorbs excrement such as urine, and a liquid-permeable core-wrapping sheet 25 that covers the absorbent core 24 from both the skin side and the non-skin side in the thickness direction. Examples of suitable materials for the core-wrapping sheet 25 include a tissue paper, a nonwoven fabric, and the like. However, the core-wrapping sheet 25 is not essential.

The absorbent body 21 is arranged extending over the front portion 3, the crotch portion 5, and the back portion 7. The absorbent core 24 of one or more embodiments has a substantially hourglass shape in a plan view as an example of a predetermined shape. The liquid-absorbent material that constitutes the absorbent core 24 can be made of liquid-absorbent fibers (e.g., pulp fibers) or liquid-absorbent granules (e.g., a superabsorbent polymer, so-called SAP), for example. The liquid-absorbent material may also include a liquid-absorbent material other than the liquid-absorbent fibers and the liquid-absorbent granules.

The side flaps 14 are portions located on two widthwise side portions of the central band-shaped region 12. The side flaps 14 are formed extending over the front portion 3, the crotch portion 5, and the back portion 7 (see FIG. 1). The widthwise length (width) of the side flaps 14 in the crotch portion 5 is smaller than the widthwise length (width) of the side flaps 14 in the front portion 3 and the back portion 7. The side flaps 14 are each mainly constituted by skin-side sheets 26 and the back sheet 23 (see FIG. 2). The skin-side sheets 26 are skin-side members that are formed extending over the front portion 3, the crotch portion 5, and the back portion 7, and are constituted by a nonwoven fabric, for example. The skin-side sheets 26 are members that constitute the leg side gathers 17 (barrier cuffs), and the outer portions of the skin-side sheets 26 (portions outside of joining portions 26A indicated by dashed lines in FIG. 1) constitute the side flaps 14.

In the central band-shaped region 12, at least in the crotch portion 5 are provided with a pair of leg elastic members 28 (e.g., elastic strings) that are capable of stretching and contracting in the longitudinal direction, between the skin-side sheets 26 and the top sheet 22. The leg elastic members 28 are members that give stretchability to the central band-shaped region 12 in the crotch portion 5, and are attached in a state of being stretched in the longitudinal direction. Accordingly, the leg elastic members 28 apply a contractive force acting in the longitudinal direction to the crotch portion 5 of the central band-shaped region 12.

The pair of side flaps 14 are each provided with a leg-gather elastic member 15 that stretches and contracts in the longitudinal direction. The leg-gather elastic members 15 are elastic members that stretch and contract in the longitudinal direction, and are members that give stretchability to the leg openings while the diaper 1 is put on. Specifically, the leg-gather elastic members 15 are leg elastic members that allow the leg portion of the diaper 1 to fit to the legs of the wearer. The leg-gather elastic members 15 may be, for example, a band-shaped elastic sheet having stretchability, a plurality of elastic strings, or the like. The leg-gather elastic members 15 give stretchability to the skin-side sheets 26 and the back sheet 23 of the crotch portion 5, thereby constituting the leg gathers 16.

The leg side gathers 17 are barrier cuffs for preventing the leakage of liquids through gaps around the legs. The pair of leg side gathers 17 extend along the longitudinal direction over the front portion 3, the crotch portion 5, and the back portion 7 (see FIG. 1). The leg side gathers 17 are formed inside of the side flaps 14 so as to cover the two edges of the central band-shaped region 12.

The leg side gathers 17 (barrier cuffs) are mainly constituted by portions of the skin-side sheet 26 that are inside in the width direction (see FIG. 2). The inner edges of the skin-side sheets 26 in the crotch portion 5 have stretchability due to a leg-side-gather elastic members 18 such as elastic strings. The skin-side sheets 26 are each joined along the longitudinal direction in the joining portion 26A that is between the central band-shaped region 12 and the side flap 14. While the diaper 1 is put on, due to the stretchability of the leg-side-gather elastic member 18, the region inside in the width direction with respect to the joining portion 26A in the skin-side sheet 26 rises toward the wearer's skin at the joining portion 26A, thereby suppressing lateral leakage of excrement or the like.

The back portion 7 has a back waist portion 7B positioned on the wearer's back waist while the diaper is put on (see FIG. 1). The back waist portion 7B is a portion extending from the longitudinal outer end of the back portion 7 to the longitudinal inner end of portions where the side flaps 14 each extend in the width direction. The fastening tapes 30 are arranged on two widthwise side portions of the portions where the side flaps 14 each extend in the width direction, in the back waist portion 7B of the diaper 1 (see FIG. 1). Further, by engaging the fastening tapes 30 with later-described target tapes 29 (FIG. 1), a waist opening and a leg opening of the diaper 1 are formed, making it possible to fix the position of the diaper 1 with respect to the wearer's body (trunk).

The front portion 3 has a front waist portion 3F positioned on the wearer's front waist while the diaper is put on (see FIG. 1). The front waist portion 3F is a region corresponding to the above-described back waist portion 7B while the diaper is put on. The target tapes 29 are provided in the front waist portion 3F of the central band-shaped region 12. The target tapes 29 are each arranged on the non-skin side of the exterior sheet 27 of the front waist portion 3F. The target tapes 29 are members that can respectively engage with the fastening tapes 30, and are formed by nonwoven fabric, for example. The target tapes 29 constitute a target region for engagement with the fastening tapes 30. It should be noted that, instead of the target tapes 29 being arranged on the non-skin side of the exterior sheet 27, the target region may be directly formed on the outermost piece of nonwoven fabric that constitutes the exterior sheet 27. Also, the diaper 1 is put on by engaging the fastening tapes 30 with the target tapes 29.

As shown in FIGS. 1 and 2, the diaper 1 of one or more embodiments includes a feces indicator 40 and urine indicators 50 on the non-skin side in the thickness direction with respect to the absorbent body 21, the feces indicator 40 being an indicator that visually changes a color due to contact with feces, the urine indicators 50 each being an indicator that visually changes a color due to contact with urine. The feces indicator 40 and the urine indicators 50 are separated from each other in the width direction and are arranged extending along the longitudinal direction, in a band-like shape. But the feces indicator 40 and the urine indicators 50 does not have to be separated in the width direction. In addition, the indicators may be arranged discontinuously in the longitudinal direction.

The urine indicators 50 are indicators including a pH indicator which is employed in a conventional common diaper. For example, in the urine indicators 50, the pH of urine is used as a reaction factor (urine-indicator reaction factor), and the discharge of urine is detected when the urine indicators 50 exhibit a predetermined reaction (e.g., color reaction) upon contact with urine. The feces indicator 40 will be described later in detail.

Principle of Feces Indicator 40

The feces indicator 40 is a feces indicator for an absorbent article such as the diaper 1, and detects the excretion of feces by exhibiting a predetermined reaction (e.g., color reaction) upon contact with a predetermined reaction factor (feces-indicator reaction factor) that is contained in feces. In one or more embodiments, the feces indicator 40 includes a chemical component that detects a biological substance in feces, and the response of the chemical component to feces is different from the response to urine, making it possible to detect only the excretion of feces.

For example, in the case where a protein is a target biological substance (feces-indicator reaction factor) to be detected by the chemical component that is contained in the feces indicator 40, it is possible to use a pH indicator as the chemical component. Generally, a protein has a structure in which amino acids are polymerized, and has acidic and basic functional groups at both ends of the main chain and the side chains of the protein. Therefore, in the case where a certain amount or more of the protein is present, it is possible to make the pH indicator change its color (protein error method). In one or more embodiments, the pH indicator responds to feces by detecting undigested protein derived from food in feces, protein secreted from intestinal bacteria, or the like.

As a specific pH indicator, for example, it is possible to use tetraphenol blue. In this case, if the protein is present, the pH indicator binds to a free amino group in the protein to form a salt-like blue compound, and exhibits a blue color corresponding to a pH that is higher than the true pH. Accordingly, when the feces indicator 40 including tetraphenol blue comes into contact with feces, the feces indicator changes color from yellow to blue. It should be noted that, in order to make it easier to change the color of the pH indicator, the pH may be set in advance to the acidic side at approximately pH 3. Therefore, the pH indicator may include a citrate buffer or the like.

In this manner, by using a predetermined pH indicator, it is possible to make the pH indicator change color in response to a protein, without the occurrence of color change caused by a change in the pH of urine or feces itself. It should be noted that the pH indicator used in the protein error method is not limited to the above-described tetraphenol blue, and it is possible to use other pH indicators. For example, it is possible to use bromophenol blue, bromocresol green, thymolphthalein, and the like, or other indicators. Furthermore, the pH indicator may be safe for the skin and may have an excellent storage properties with respect to moisture or sunlight.

Further, in the feces indicator 40, the chemical component included in the feces indicator 40 may respond to feces and may not respond to urine so as not to erroneously detect whether the excrement is feces or urine. Therefore, the feces indicator 40 in one or more embodiments exhibits a reaction such as a color reaction in response to a feces-indicator reaction factor (protein or the like) which has a predetermined concentration or higher. In the case where the concentration of the feces-indicator reaction factor is lower than the predetermined concentration, it is less likely to cause the reaction.

Generally, protein is not included in the urine of a healthy person, and even in the case of a non-healthy person, the amount of protein in the urine is less than 10,000 mg/L. Therefore, in one or more embodiments, with the protein error method using a pH indicator, the feces indicator 40 responds to preferably 150 mg/L or more of protein, responds to more preferably 5,000 mg/L or more of protein, and responds to even more preferably 10,000 mg/L or more of protein. For example, under the condition where bromophenol blue is used as the chemical component, in the case where the feces indicator 40 responds to 150 mg/L or more of protein, the amount of the pH indicator applied per 1 cm$^2$ in the feces indicator 40 may be 16.3 µg, in the case where the feces indicator 40 responds to 5,000 mg/L or more of protein, the amount of the pH indicator applied per 1 cm$^2$ in the feces indicator 40 may be 0.5 µg, and in the case where the feces indicator 40 responds to 10,000 mg/L or more of protein, the amount of the pH indicator applied per 1 cm$^2$ in the feces indicator 40 may be 0.25 µg. It should be noted that setting the amount of the pH indicator applied to 17.0 µg or less enhances the safety of the feces indicator 40 for the wearer of the absorbent article.

In one or more embodiments, by adjusting the amount of the pH indicator applied as described above, the range in which the feces indicator 40 can react to urine can be made relatively narrower compared with the range in which the feces indicator 40 can react to feces. In other words, the reaction of the feces indicator 40 to feces can be made different from the reaction of the feces indicator 40 to urine. This enables to make the feces indicator 40 difficult to react to urine.

Further, a reaction factor of the feces indicator 40 is not limited to the protein described above. For example, it is acceptable that the feces indicator 40 reacts to the intestinal bacteria contained in the feces, the ionic strength of feces that correlates with the specific gravity of the feces, and a feces-derived substance such as bilirubin, which is a bile pigment. These components are generally not included in urine or are contained in a very small amount or a very small specific gravity in urine compared with feces. Accordingly, in the same manner as in the case of using a protein as a reaction factor, the feces indicator 40 is less likely to react to urine and is more likely to react to feces. Therefore, it is possible to detect the feces excreted in the diaper 1 with high accuracy.

Specific Configuration of Feces Indicator 40

The feces indicator 40 is formed by applying an adhesive (e.g., hot-melt adhesive HMA) containing the chemical component (e.g., pH indicator) described above to the skin-side surface of the back sheet 23 of the diaper 1. In one or more embodiments, as shown in FIG. 1, the feces indicator 40 is formed by applying a hot-melt adhesive (HMA) using a coater to a strip-shaped (or linear) region which extends along the longitudinal direction over the front portion 3, the crotch portion 5, and the back portion 7. According to the above-described coater application, it is possible to form the feces indicator 40 whose film thickness is uniform and that has little unevenness, making it possible to enhance the detection accuracy of feces. Further, it is possible to reduce manufacturing costs. It should be noted that it is possible to form the urine indicator 50 in the same manner.

Alternatively, the feces indicator 40 may be formed by mixing a chemical component with ink and performing print coating on the back sheet 23 or the core-wrapping sheet 25 with the mixture. Alternatively, the feces indicator 40 may be formed as follow: a filter paper or a nonwoven fabric impregnated with the chemical component is joined and fixed to the back sheet 23 or the core-wrapping sheet 25 with a hot-melt adhesive (HMA) or by ultrasonic welding.

Color Reaction of Feces Indicator 40 and Urine Indicator 50

As shown in FIG. 1, in one or more embodiments, the feces indicator 40 and the urine indicator 50 are provided in a strip-like shape extending along the longitudinal direction while being spaced apart from each other in the width direction. The feces indicator 40 is an indicator that visually changes a color due to contact with feces (undergoes a so-called color reaction). The feces indicator 40 has a pre-change color which is a color before the color change and a post-change color which is a color after the color change due to contact with feces. The urine indicator 50 is an indicator that visually changes a color due to contact with urine (undergoes a so-called color reaction). The urine indicator 50 similarly has a pre-change color which is a color before the color change and a post-change color which is a color after the color change due to contact with urine.

In the case where an absorbent article such as a diaper includes both of the urine indicator 50 and the feces indicator 40 that exhibit a color reaction and which notify a user (for example, a person replacing the absorbent article) that defecation or urination has occurred, there is a possibility of making the user think that the followings is difficult to remember and a risk of making the user think that remembering the followings is troublesome: the color of each of the indicators (40, 50) before putting on the absorbent article; or the color to which each of the indicators will change.

Figure 3A:
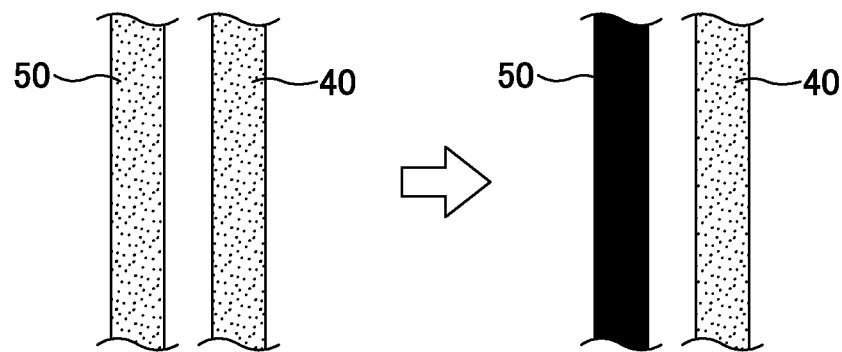
FIGS. 3A, 3B, and 3C each show a state of parts of a feces indicator 40 and a urine indicator 50 in FIG. 1 viewed from a non-skin side of the diaper 1.
Figure 3B:
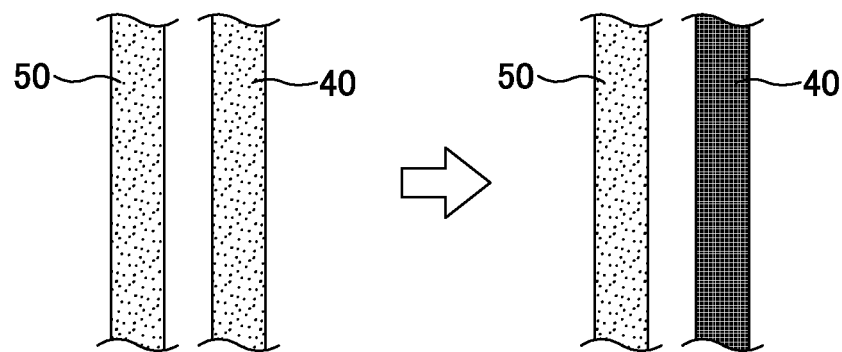
Figure 3C:
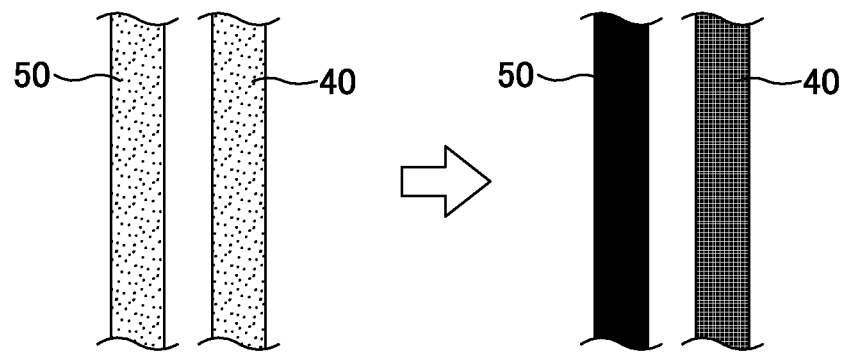

In contrast, in one or more embodiments, the pre-change color and the post-change color of each of the feces indicator 40 and the urine indicator 50 have the following configurations. FIGS. 3A, 3B, and 3C each show a state of parts of the feces indicator 40 and the urine indicator 50 in FIG. 1 viewed from the non-skin side of the diaper 1. The left diagram of FIG. 3A shows a state before the colors of the feces indicator 40 and the urine indicator 50 are changed (that is, before use). As shown in the drawing, in one or more embodiments, the pre-change color of the feces indicator 40 and the pre-change color of the urine indicator 50 are similar (analogous) colors. In the right diagram of FIG. 3A, it can be found that the urine indicator 50 changes the color in response to urine, which results in the feces indicator 40 and the urine indicator 50 that had similar colors no longer having similar colors. Accordingly, the person replacing the diaper 1 can recognize that urination has occurred.

In FIG. 3B, before use, the pre-change colors of the feces indicator 40 and the urine indicator 50 are similar colors (left diagram of FIG. 3B). In the right diagram of FIG. 3B, it is found that the feces indicator 40 changes the color in response to feces, which results in the colors of the feces indicator 40 and the urine indicator 50 no longer having similar colors. Accordingly, the person replacing the diaper 1 can recognize that defecation has occurred.

In FIG. 3C, the pre-change colors of the feces indicator 40 and the urine indicator 50 are similar colors (the left diagram of FIG. 3C). But, the feces indicator 40 and the urine indicator 50 respectively detect defecation and urination, and in the right diagram of FIG. 3C, the indicators (40, 50) change their colors from the pre-change color. Then, the post-change colors of the feces indicator 40 and the urine indicator 50 are dissimilar colors. Accordingly, the person replacing the diaper 1 can recognize that both defecation and urination have been occurred. In this way, the fact that the colors of the two indicators (40, 50) are no longer the similar colors makes it possible for the person replacing the diaper 1 to recognize the occurrence of the color change, even when the replacing person does not remember the pre-change colors of the indicators (40, 50). This makes it possible for the replacing person to notice at least that defecation or urination has occurred.

Similar Color and Dissimilar Color

Here, the degree of the similar colors and the degree of the dissimilar colors of the indicators (40, 50) will be described. In the case where the pre-change color and the post-change color of each of the feces indicator 40 and the urine indicator 50 are specified as the closest hues among the 24 color hues of the Ostwald color wheel, the degree of the similar colors is that the colors have an identical hue in the Ostwald color wheel, or that the colors are in a range in which the difference between their color numbers is less than 6. Their color numbers may be in a range separated by one from each other. The colors in such a range makes it possible for an observer having ordinary attention to recognize that the colors are visually similar. Further, the degree of the dissimilar colors is that their color numbers in the Ostwald color wheel are apart by 6 or more from each other. When the colors are apart by 6 or more in color number from each other, the difference in color tone becomes clear visually, making it easier for an observer to identify the difference in color between the indicators (40, 50).

In addition, concerning specifying the pre-change color or the post-change color of the feces indicator 40 and the urine indicator 50 to the hue in the Ostwald color wheel, the specifying is performed by comparing by the eyes the pre-change color (and the post-change color) with the hue of the Ostwald color wheel and determining the color number of the closest hue. In the case where the color tone is vague and the determination is difficult to be made by the eye, the following method is also acceptable: converting the color of the pre-change color (or post-change color) into colorimetric number using a colorimeter (e.g., a Chroma Meter "CR-300" manufactured by Minolta Corporation), and based on the resultant brightness and saturation of the color, specifying the characteristics of the color among colors having similar color tone by comparing the hue to the Ostwald color wheel.

Modifications of Pre-Change Color and Post-Change Color

The configuration of the pre-change colors and the post-change colors of the feces indicator 40 and the urine indicator 50 will be described using other Modifications.

Figure 4:
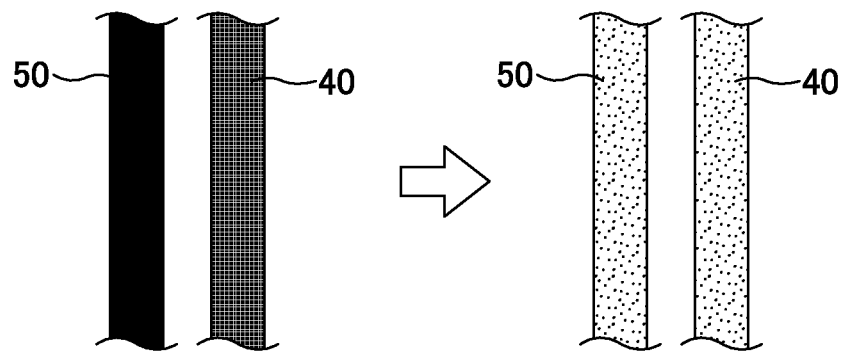
FIG. 4 is a diagram illustrating a Modification of the color changes of the feces indicator 40 and the urine indicator 50.
Figure 5:
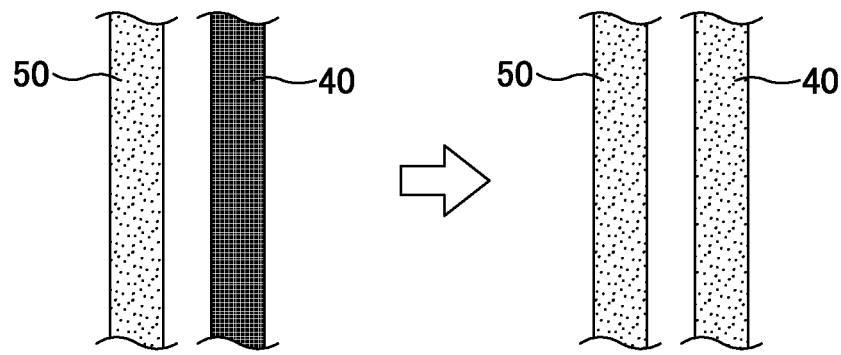
FIG. 5 is a diagram illustrating a Modification of the color changes of the feces indicator 40 and the urine indicator 50.
Figure 6:
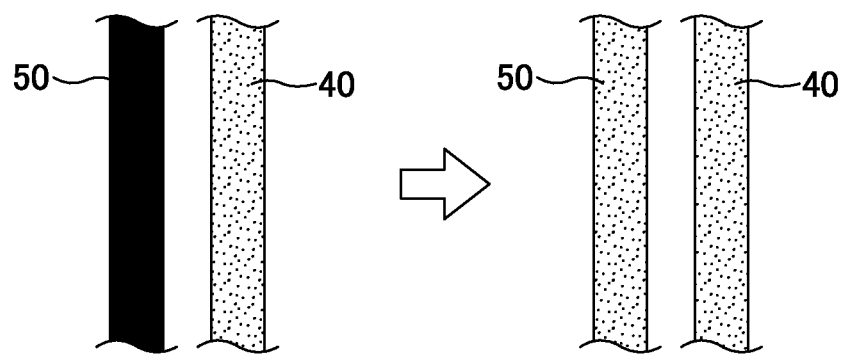
FIG. 6 is a diagram illustrating a Modification of the color changes of the feces indicator 40 and the urine indicator 50.

FIGS. 4 to 6 are diagrams illustrating Modifications of color changes of the feces indicator 40 and the urine indicator 50, and show a state of parts of the feces indicator 40 and the urine indicator 50 viewed from the non-skin side of the diaper 1. The left diagram of FIG. 4 shows a state before the colors of the feces indicator 40 and the urine indicator 50 change (that is, before use). In FIG. 4, the pre-change colors of the feces indicator 40 and the urine indicator 50 before use are dissimilar colors to each other. In the right diagram of FIG. 4, the feces indicator 40 and the urine indicator 50 respectively detect defecation and urination, and consequently the post-change color of the feces indicator 40 and the post-change color of the urine indicator 50 are similar colors. Accordingly, even when the person replacing the diaper 1 does not remember the colors (that is, the pre-change colors) of the indicators (40, 50) at the time of putting on the diaper 1 or even when the replacing person does not recognize what colors will the colors of the indicators change to after the reaction, the colors of both indicators (40, 50) having dissimilar colors becoming similar colors makes it possible for the replacing person to recognize the occurrence of the color change. This makes it possible to recognize that defecation or urination has occurred.

Similarly, the left diagram of FIG. 5 shows a state before the colors of the feces indicator 40 and the urine indicator 50 change (that is, before use). In FIG. 5, the pre-change colors of the indicators (40, 50) before use of the diaper 1 are dissimilar colors. However, only defecation has occurred, and the feces indicator 40 detects the feces, and the color (post-change color) of the feces indicator 40 and the color (pre-change color) of the urine indicator 50 become similar colors (right diagram of FIG. 5). Even when the person replacing the diaper 1 does not remember the color of the feces indicator 40 before defecation, by changing to similar colors the colors of both indicators (40, 50) which do not have similar colors, it is possible for the replacing person to recognize the occurrence of the color change and to recognize that defecation has occurred.

Similarly, the left diagram of FIG. 6 shows a state before the colors of the feces indicator 40 and the urine indicator 50 changes (that is, before use). In FIG. 6, the pre-change colors of the indicators (40, 50) before use of the diaper 1 are dissimilar colors. However, only urination has occurred, and the urine indicator 50 detects the urine, and the color (post-change color) of the urine indicator 50 and the color (pre-change color) of the feces indicator 40 become similar colors (right diagram of FIG. 6). Accordingly, even when the replacing person does not remember the color of the urine indicator 50 before urination, by changing to similar colors the colors of both indicators (40, 50) which do not have similar colors, it is possible for the replacing person to recognize the occurrence of the color change and to recognize that urination has occurred.

As shown in FIGS. 3A to 6, in order for the person replacing the diaper 1 to recognize the occurrence of the color change, the following configuration is required: either one of the pre-change color and the post-change color of the feces indicator 40 and either one of the pre-change color and the post-change color of the urine indicator 50 are similar colors; and the other color of the pre-change color and the post-change color of the feces indicator 40 and the other color of the pre-change color and the post-change color of the urine indicator 50 are dissimilar colors.

That is, by setting the colors of both indicators (40, 50) to the similar colors before or after the reaction, it is possible for the person replacing the diaper 1 to recognize that defecation, urination, or both have occurred even when the replacing person does not remember the actual colors of the indicators (or what colors will the colors of the indicators change to). For example, when the indicators having similar colors before use no longer have the similar colors, it triggers that the person replacing the diaper 1 can recognize the occurrence of the color change and can recognize that at least defecation or urination has occurred. Conversely, when the indicators not having similar colors to each other before use become similar colors, it triggers that the person replacing the diaper 1 can recognize the occurrence of the color change and can recognize that at least defecation or urination has occurred. Further, by setting to dissimilar colors either of the pre-change colors of each of the feces indicator 40 and the urine indicator 50 (which are before the colors become similar colors) or the post-change colors of each of the feces indicator 40 and the urine indicator 50 (which are after the colors have changed from similar colors), it is possible to avoid that the colors of the indicators (40, 50) change from the similar color to the similar color. This makes it possible for the replacing person to recognize the color change without confusion.

Further, in the feces indicator 40, as shown in FIGS. 3A, 3B, 3C, 4, and 6, the pre-change color which is a color before the reaction of the feces indicator 40 and the post-change color which is a color after the contact with the feces may be the dissimilar colors. In addition to the color difference between the feces indicator 40 and the urine indicator 50, the pre-change color and the post-change color of the single feces indicator 40 being dissimilar colors makes clear the color difference before and after the reaction. This makes it possible for the person replacing the diaper 1 to reliably recognize that defecation has occurred.

Figure 7:
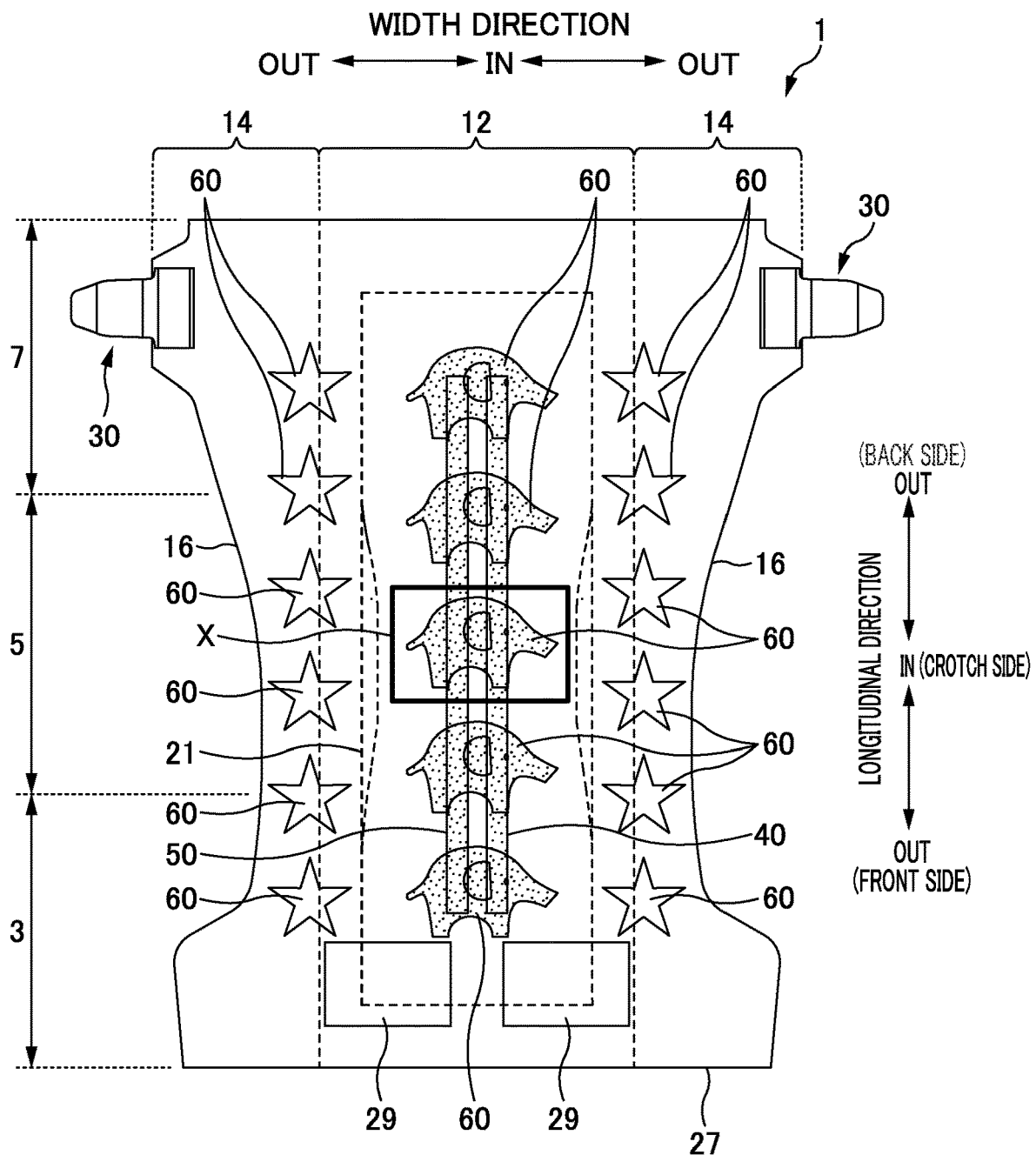
FIG. 7 is a plan view of the tape-type disposable diaper 1 having graphics 60, in the unfolded and stretched state when viewed from the non-skin side.
Figure 8A:
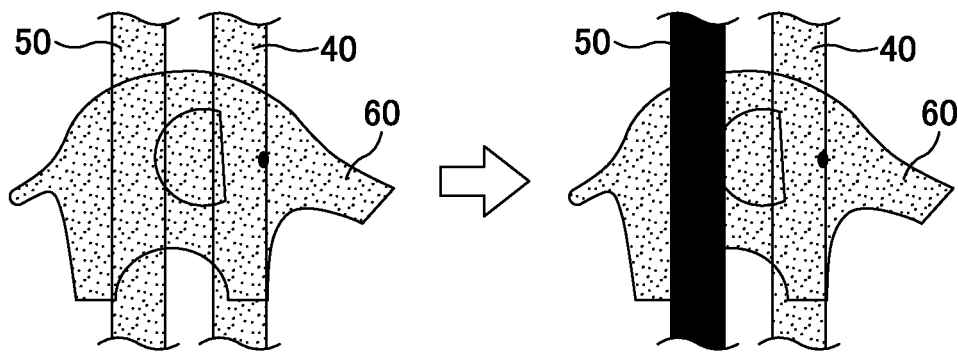
FIGS. 8A, 8B, and 8C are enlarged views of a region X in FIG. 7.
Figure 8B:
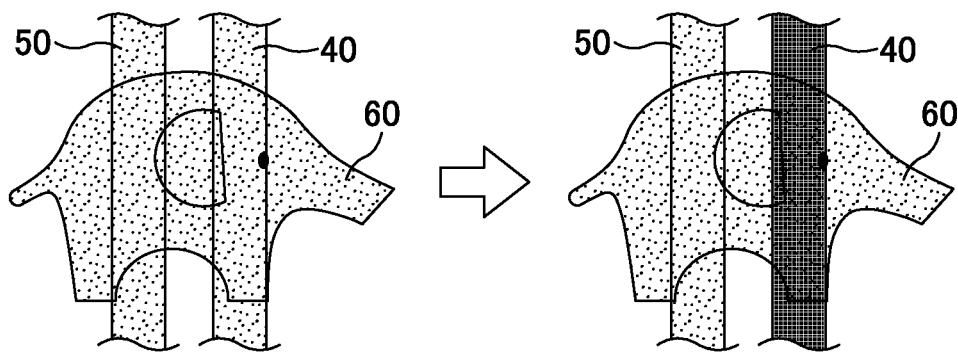
Figure 8C:
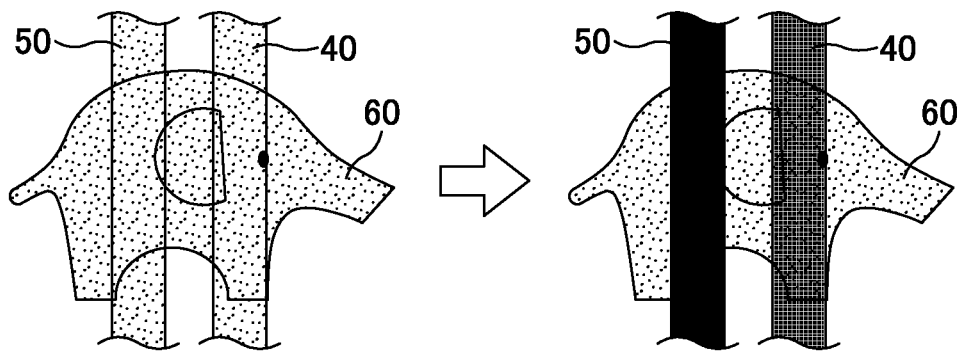
Figure 9:
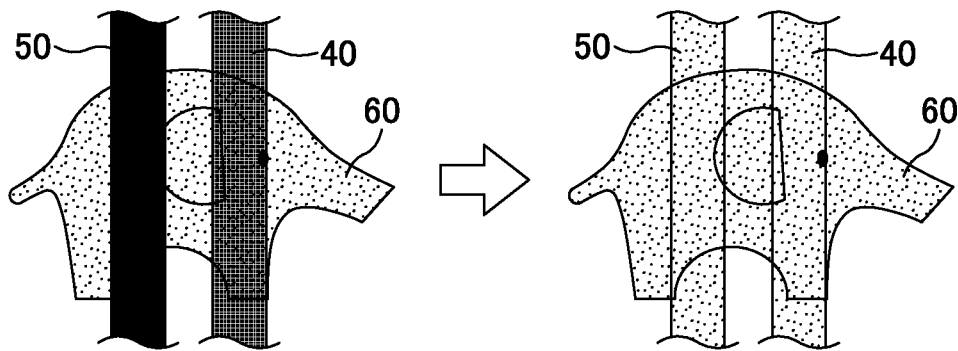
FIG. 9 is a diagram illustrating a Modification of the relationship between the color of the graphic 60 and the color changes of the feces indicator 40 and the urine indicator 50.
Figure 10:
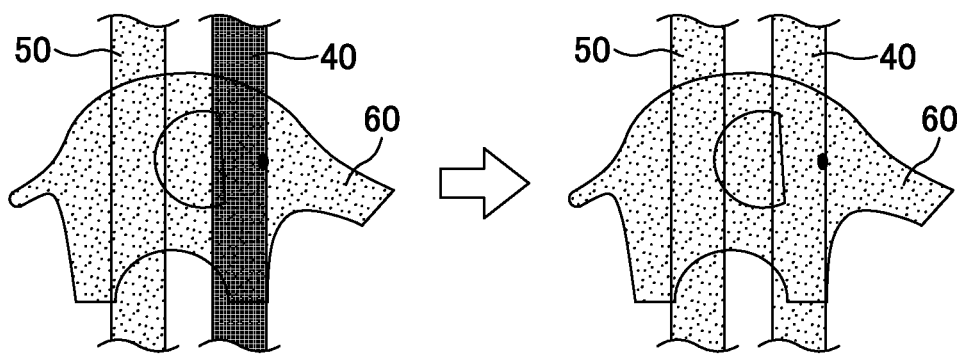
FIG. 10 is a diagram illustrating a Modification of the relationship between the color of the graphic 60 and the color changes of the feces indicator 40 and the urine indicator 50.
Figure 11:
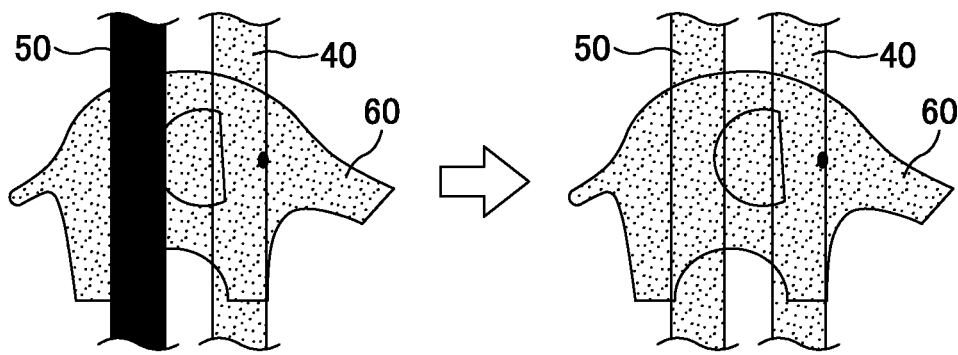
FIG. 11 is a diagram illustrating a Modification of the relationship between the color of the graphic 60 and the color changes of the feces indicator 40 and the urine indicator 50.

FIG. 7 is a plan view of the tape-type disposable diaper 1 having graphics 60, in the unfolded and stretched state when viewed from the non-skin side. FIGS. 8A, 8B, and 8C are enlarged views of a region X in FIG. 7. FIGS. 9 to 11 are each a diagram illustrating a Modification of the relationship between the color of the graphic 60 and the color changes of the feces indicator 40 and the urine indicator 50.

The diaper 1 includes the back sheet 23 that is located on the non-skin side in the thickness direction with respect to the feces indicator 40 and the urine indicator 50 (see FIG. 2). Here, as shown in FIG. 7, the back sheet 23 has the graphics 60, and the user can visually recognize the graphics 60 from the non-skin side of the diaper 1. It should be noted that the graphics 60 is not limited to the graphic shown in FIG. 7, and may be any graphic, text character, or the like. Further, the diaper 1 shown in FIG. 7 is in a state before use, and the pre-change color of the feces indicator 40, the pre-change color of the urine indicator 50, and the color tone of the graphics 60 are similar colors. Further, the graphics 60 overlap at least a part of the feces indicator 40 and the urine indicator 50 when viewed in the thickness direction.

The left diagram of FIG. 8A shows a state before use, and all of the pre-change colors of the feces indicator 40, the urine indicator 50, and the graphic 60 are similar colors. In the right diagram of FIG. 8A, the urine indicator 50 detects urine, and only the color of the urine indicator 50 changes to a dissimilar color. The colors of three items, namely the indicators (40, 50) and the graphic 60, all are similar colors before use. This can make the person replacing the diaper 1 easier to notice the color change of the urine indicator 50 and to recognize that urination has occurred.

The left diagram of FIG. 8B shows a state before use, and all of the pre-change colors of the feces indicator 40, the urine indicator 50, and the graphic 60 are similar colors. In the right diagram of FIG. 8B, the feces indicator 40 detects feces, and only the color of the feces indicator 40 changes to a dissimilar color. The colors of three items, namely the indicators (40, 50) and the graphic 60, all are similar colors before use. This can make the person replacing the diaper 1 easier to notice the color change of the feces indicator 40 and to recognize that defecation has occurred.

Similarly, the left diagram of FIG. 8C shows a state before use, and all of the pre-change colors of the feces indicator 40, the urine indicator 50, and the graphic 60 are the similar colors. In the right diagram of FIG. 8C, the feces indicator 40 and the urine indicator 50 respectively detect feces and urine, and their colors changes. Also, the post-change color of the feces indicator 40 and the post-change color of the urine indicator 50 are dissimilar colors to each other. The colors of three items, namely the indicators (40, 50) and the graphic 60, all are similar colors before use. And, that the colors of the feces indicator 40 and urine indicator 50 are no longer the similar colors makes it possible to recognize the occurrence of the color change. This makes the replacing person easier to determine that both defecation and urination have occurred.

In the Modification shown in FIG. 9, the indicators and the graphic are provided such that, before use, the pre-change color of the feces indicator 40, the pre-change color of the urine indicator 50, and the color of the graphic 60 are dissimilar colors to each other (left diagram of FIG. 9). In the right diagram of FIG. 9, the feces indicator 40 and the urine indicator 50 respectively detect feces and urine, and their colors change to the post-change colors. Consequently, all of the feces indicator 40, the urine indicator 50, and the graphic 60 have the similar colors. By changing to similar colors the colors of the indicators (40, 50) and the graphic 60 which have dissimilar colors before use, it makes the person replacing the diaper 1 easier to recognize the occurrence of the color change. This makes it possible to recognize that both defecation and urination have occurred.

In the Modification shown in FIG. 10, the indicators and the graphic provided such that, before use, the pre-change color of the urine indicator 50 and the color of the graphic 60 are similar colors and the pre-change color of the feces indicator 40 is a dissimilar color (left diagram of FIG. 10). Further, in the right diagram of FIG. 10, the feces indicator 40 detects feces and its color changes to the post-change color. Consequently, all of the feces indicator 40, the urine indicator 50, and the graphic 60 have similar colors. This make the replacing person easier to recognize the occurrence of the color change of the feces indicator 40, making it possible to recognize that the defecation has occurred.

In the Modification shown in FIG. 11, in contrast, the indicators and the graphic provided such that, before use, the pre-change color of the feces indicator 40 and the color of the graphic 60 are similar colors, and the pre-change color of the urine indicator 50 is a dissimilar color (left diagram of FIG. 11). Further, in the right diagram of FIG. 11, the urine indicator 50 detects urine and its color changes to the post-change color. Consequently, all of the feces indicator 40, the urine indicator 50, and the graphic 60 have similar colors. This make the replacing person easier to recognize the occurrence of the color change of the urine indicator 50, making it possible to recognize that the urination has occurred.

As described above, in order for the person replacing the diaper 1 to recognize the occurrence of the color change, the following configuration is required: either one of the pre-change color and the post-change color of the feces indicator 40 and either one of the pre-change color and the post-change color of the urine indicator 50, and the color tone of the graphic 60 are similar colors; and the graphic 60 overlap at least one of the feces indicator 40 or the urine indicator 50 when viewed in the thickness direction. The colors of three items, namely the feces indicator 40, the urine indicator 50, and the graphic 60, being similar colors makes the person replacing the diaper 1 easier to notice the similarity of the colors. In other words, in the case where the colors of three items, namely the feces indicator 40, the urine indicator 50, and the graphic 60 of the back sheet 23, are similar colors before use, only changing at least the color of the urine indicator or the feces indicator makes the replacing person easier to notice the color change. This makes it possible to recognize that at least urination or defecation has occurred. Further, in the case where neither of the colors of three items, namely the feces indicator 40, the urine indicator 50, and the graphic 60, are similar colors before use, making the colors of the indicators (40, 50) and the graphic 60 be similar colors after the feces indicator 40 and the urine indicator 50 react with the feces and urine makes the replacing person easier to recognize the development of the color change. This makes it easier to determine that urination and defecation have occurred.

Further, the feces indicator 40 and the urine indicator 50 are intended to be visually recognized from the outside of the diaper 1 through the back sheet 23 and the exterior sheet 27. Accordingly, a material having a high transparency may be used as the back sheet 23 so as to enhance visibility. However, when the transparency is too high, there is a risk that excrement may be seen through from the outside of the diaper 1. Therefore, in one or more embodiments, the light transmittance of the back sheet 23 is 30% to 80%. As for the exterior sheet 27, in one or more embodiments, the exterior sheet 27 has a predetermined light transmittance so that visual changes of the indicators (40, 50) is easily recognized. Accordingly, in one or more embodiments, the light transmittance of the exterior sheet 27 is 50% or more. This makes the person replacing the diaper 1 easier to recognize the degrees of color changes of the indicators (40, 50). It should be noted that the light transmittance can be measured by, for example, a test method according to JIS Z 8722 or the like.

Figure 12:
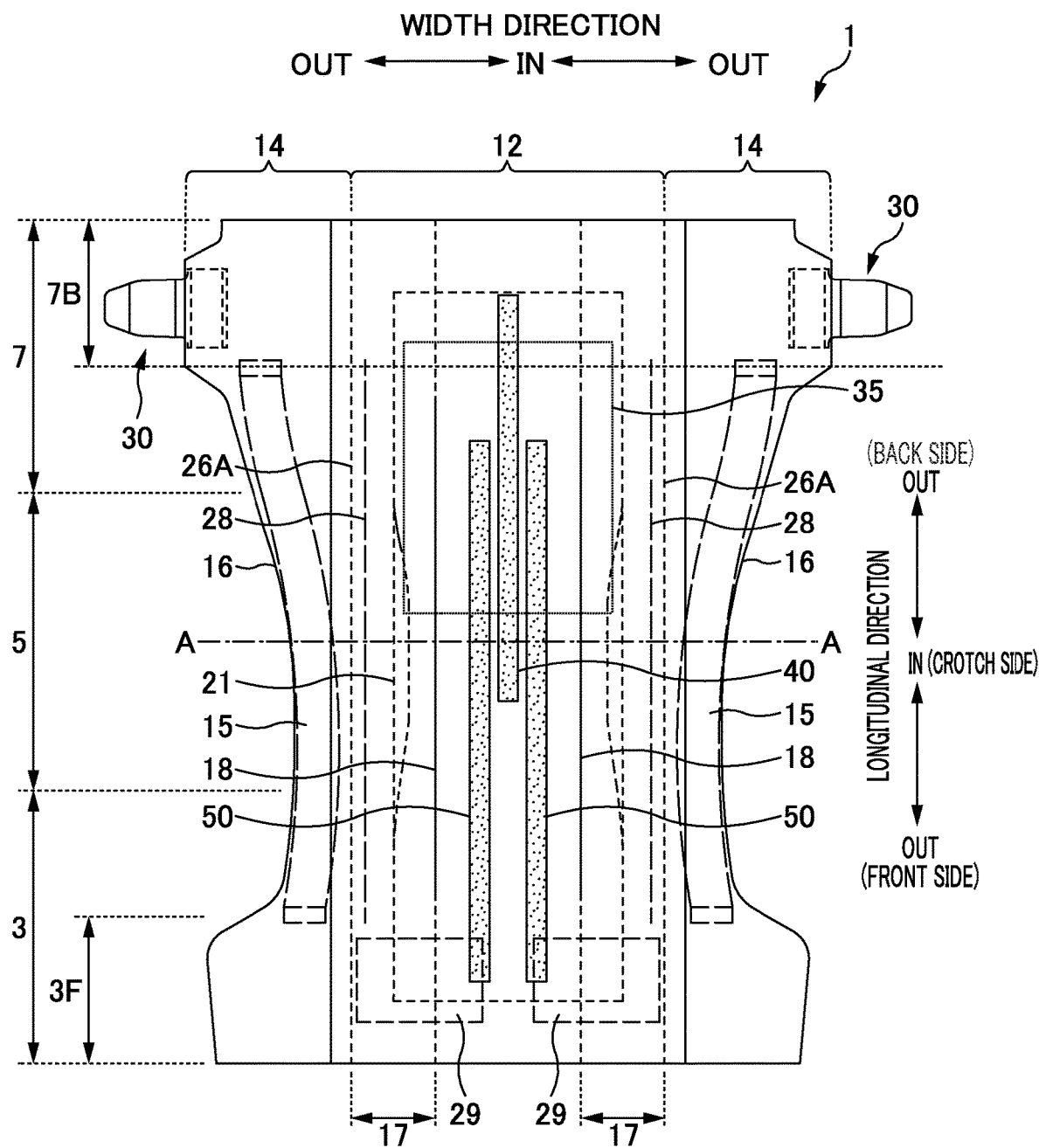
FIG. 12 is a plan view of another example of the tape-type disposable diaper 1 in the unfolded and stretched state.

FIG. 12 is a plan view of another example of the tape-type disposable diaper 1 in the unfolded and stretched state. In one or more embodiments, the diaper 1 has the feces indicator 40 in the central portion in the width direction, and is provided with a pair of urine indicators 50 spaced apart outward in the width direction with respect to the feces indicator 40. The line A-A is the center line of the diaper 1 in the longitudinal direction, and the feces indicator 40 is arranged so as to straddle the longitudinal central portion of the diaper 1.

The longitudinal central portion of the diaper 1 is a position where the diaper 1 is folded one time, and the front side and the back side of the diaper 1 are distinguished with reference to the position. Accordingly, the feces indicator 40 is arranged so as to cover both of the front side and the back side of the diaper 1 in the longitudinal direction, making it easier to detect feces in the case of defecation which is made not only when the user is in a lying-down state but also when the user is in a standing state or the like.

Further, as shown in FIG. 12, the feces indicator 40 overlaps the back waist portion 7B when viewed in the thickness direction. Since the feces have low moisture unlike urine, it is advantageous to arrange the feces indicator close to the back-side in order for the feces indicator to react with the low moisture. Further, as in the feces indicator 40 shown in FIG. 12, arranging the feces indicator 40 to extend to the further outside in the longitudinal direction increases a possibility that the feces does not reach the longitudinal outermost side end (back-side end) of the feces indicator 40 and the pre-change color remains. After the occurrence of defecation, the feces indicator 40 has the two-color structure composed of the pre-change color portion and the post-change color portion, and it makes the person replacing the diaper 1 easier to recognize the development of the color change.

Color Difference Before and After Change of Each Indicator

The feces indicator 40 and the urine indicator 50 each have the pre-change color and the post-change color, but the color difference of the colors can be set as follows.

First, among the 24 color hues of the Ostwald color wheel, the hues which are respectively closest to the pre-change color and the post-change color of the urine indicator 50 are specified. The hue specified as the pre-change color of the urine indicator 50 is defined as a first hue, and the hue specified as the post-change color of the urine indicator 50 is defined as a second hue. Similarly, among the 24 color hues of the Ostwald color wheel, the hues which are respectively closest to the pre-change color and the post-change color of the feces indicator 40 are specified. The hue specified as the pre-change color of the feces indicator 40 is defined as a third hue, and the hue specified as the post-change color of the feces indicator 40 is defined as a fourth hue. In such a case, the difference in color number between the first hue and the second hue in the Ostwald color wheel may be larger than the difference in color number between the third hue and the fourth hue. A large hue difference means a large color change, and a large color change makes it easier to recognize the change. That the color change of the urine indicator 50 before and after the reaction is larger than the color change of the feces indicator 40 before and after the reaction enables to more easily recognize the occurrence of urination, making it possible to preferentially detect urine.

Similar to the above, in the case where, among the 24 color hues of the Ostwald color wheel, the pre-change color and the post-change color of the urine indicator 50 are respectively specified as a first hue and a second hue, and the pre-change color and the post-change color of the feces indicator 40 are respectively specified as a third hue and a fourth hue, the difference in color number between the third hue and the fourth hue (that is, the color difference from the pre-change color to the post-change color of the feces indicator 40) may be larger than the difference in color number between the first hue and the second hue (that is, the color difference from the pre-change color to the post-change color of the urine indicator 50). That the color change of the feces indicator 40 before and after the reaction is larger than the color change of the urine indicator 50 before and after the reaction allows the person replacing the diaper 1 to more easily recognize that defecation has occurred, making it possible to preferentially detect feces.

In addition, similarly, in the case where, among the 24 color hues of the Ostwald color wheel, the pre-change color and the post-change color of the urine indicator 50 are respectively specified as a first hue and a second hue, and the pre-change color and the post-change color of the feces indicator 40 are respectively specified as a third hue and a fourth hue, the difference in color number between the first hue and the second hue (that is, the color difference from the pre-change color to the post-change color of the urine indicator 50) may be equal to the difference in color number between the third hue and the fourth hue (that is, the color difference from the pre-change color to the post-change color of the feces indicator 40). That the color changes of the urine indicator 50 and the feces indicator 40 are substantially the same makes it easier to recognize the changes of both indicators without making the change of only one of the indicators conspicuous.

OTHER EMBODIMENTS

Although the above embodiments of the present invention have been described, but the above-described embodiments are intended to facilitate the understanding of the present invention and are not intended to limit the interpretation of the present invention. In addition, the present invention can be modified or improved without departing from the spirit thereof, and additionally, it is needless to say that equivalents thereof are included in the present invention.

In the above-described embodiments, for the purpose of making the feces (fecal fluid) excreted in the diaper 1 easier to permeate into the absorbent body 21 and to reach the feces indicator 40, the absorbent body 21 may have a low-basis-weight portion (not shown), which has a low basis weight, at the position overlapping the feces indicator 40 with respect to the longitudinal direction and with respect to the width direction. Here, the basis weight refers to the mass per unit area, and the low-basis-weight portion is a portion whose basis weight is smaller than the basis weight of regions that is adjacent to the low-basis-weight portion from the outside in the width direction. For example, in the example shown in FIG. 12, the absorbent body 21 may have a low-basis-weight portion so that the low-basis-weight portion overlaps the widthwise central portion of the absorbent body 21 and the feces indicator 40 with respect to the longitudinal direction and with respect to the width direction. This makes even highly viscous feces (fecal fluid) easier to permeate into the low-basis-weight portion of the absorbent body 21, to move from the skin side to the non-skin side, and to reach the feces indicator 40. As a result, the detectability of feces can be further enhanced.

In addition, in the above-described embodiments, the second sheet 35 is arranged between the top sheet 22 and the core-wrapping sheet 25 in the thickness direction. However, the second sheet 35 may be arranged between the absorbent body 21 and the feces indicator(s) 40, serving as a diffusion sheet that diffuses liquid. In such a case, the moisture in the feces is diffused in the lower layer of the absorbent body 21, making it possible to react the feces indicator 40 in a broader range. This makes it possible to enhance the visibility from the outer surface of the diaper 1.

Further, the top sheet 22 may have an opening. By providing an opening to the top sheet, it increases the contact area between the second sheet 35 and the feces, making it possible to enhance the permeability of the feces to the second sheet 35.

Further, in the above-described embodiments, one feces indicator 40 is arranged extending along the longitudinal direction. However, the configuration is not limited thereto, and a plurality of feces indicators 40 may be arranged side-by-side in the width direction. Arranging the plurality of feces indicators 40 makes it possible to further enhance the detection of defecation.

Although the disclosure has been described with respect to only a limited number of embodiments, those skilled in the art, having benefit of this disclosure, will appreciate that various other embodiments may be devised without departing from the scope of the present disclosure. Accordingly, the scope of the invention should be limited only by the attached claims.

REFERENCE SIGNS LIST

1: Tape-type disposable diaper (absorbent article)
3: front portion, 3F: Front waist portion, 5: Crotch portion
7: back portion, 7B: Back waist portion
12: central band-shaped region
14: side flap
15: leg-gather elastic member
16: leg gather
17: leg side gather
18: leg-side-gather elastic member
21: Absorbent body
22: Top sheet
23: back sheet
24: Absorbent core
25: Core-wrapping sheet
26: skin-side sheet
26A: Joining portion
27: Exterior sheet
28: leg elastic member
29: Target tape
30: Fastening tape
35: Second sheet
40: Feces indicator
50: urine indicator
60: graphic

What is claimed is:

1. An absorbent article having a longitudinal direction, a width direction, and a thickness direction in an unfolded state, the absorbent article comprising:
    a liquid absorbent body;
    a feces indicator that visually changes between two colors, wherein
        the feces indicator changes, on contact with feces, from a pre-feces-contact color to a post-feces-contact color;
    a urine indicator that visually changes between two colors, wherein
        the urine indicator changes, on contact with urine, from a pre-urine-contact color to a post-urine-contact color, and
        the feces indicator and the urine indicator are disposed on a non-skin side in the thickness direction with respect to the absorbent body; and
    a back sheet that has a graphic pattern and that is disposed on the non-skin side in the thickness direction with respect to the feces indicator and the urine indicator, wherein
    one of the two colors of the feces indicator is visually similar to one of the two colors of the urine indicator, whereas the other of the two colors of the feces indicator is visually dissimilar to the other of the two colors of the urine indicator,
    the graphic pattern is disposed in line in parallel with the feces indicator and the urine indicator, and at least partially overlaps at least either one of the feces indicator and the urine indicator when viewed in the thickness direction,
    the pre-feces-contact color and the pre-urine-contact color are visually similar to a color of the graphic pattern,
    at least one of the post-feces-contact color and the post-urine-contact color are visually dissimilar to the color of the graphic pattern,
    when the pre-feces-contact color, the pre-urine-contact color, the post-feces-contact color, and the post-urine-contact color are respectively specified as closest hues among 24 color hues of an Ostwald color wheel,
        a similarity degree between the one of the two colors of the feces indicator and the one of the two colors of the urine indicator is either one of:
            having an identical hue in the Ostwald color wheel, and
            being within a range in which a difference between color numbers is less than 6 in the Ostwald color wheel, and
        a dissimilarity degree between the other of the two colors of the feces indicator and the other of the two colors of the urine indicator is having color numbers that are apart by 6 or more from each other in the Ostwald color wheel.

2. The absorbent article according to claim 1, wherein the pre-feces-contact color is visually similar to the pre-urine-contact color.

3. The absorbent article according to claim 1, wherein the post-feces-contact color is visually similar to the post-urine-contact color.

4. The absorbent article according to claim 1, wherein the post-feces-contact color is visually similar to the pre-urine-contact color.

5. The absorbent article according to claim 1, wherein the pre-feces-contact color is visually similar to the post-urine-contact color.

6. The absorbent article according to claim 1, wherein the pre-feces-contact color is visually dissimilar to the post-feces-contact color.

7. The absorbent article according to claim 1, further comprises:
   an exterior sheet that forms an exterior of the absorbent article, wherein
   the back sheet has a light transmittance of 30% to 80%, and
   the exterior sheet has a light transmittance of 50% or more.

8. The absorbent article according to claim 1, wherein the feces indicator straddles a longitudinal central portion of the absorbent article.

9. The absorbent article according to claim 1, further comprises:
   a front waist portion that is fit to a wearer's front waist during usage of the absorbent article; and
   a back waist portion that is fit to a wearer's back waist during usage of the absorbent article, wherein
   the feces indicator overlaps the back waist portion when viewed in the thickness direction.

10. The absorbent article according to claim 1, wherein among the 24 color hues of the Ostwald color wheel,
    when a hue closest to the pre-urine-contact color is specified as a first hue and a hue closest to the post-urine-contact color is specified as a second hue, and
    when a hue closest to the pre-feces-contact color is specified as a third hue and a hue closest to the post-feces-contact color is specified as a fourth hue,
    a difference in color number between the first hue and the second hue is larger than a difference in color number between the third hue and the fourth hue in the Ostwald color wheel.

11. The absorbent article according to claim 1, wherein among the 24 color hues of the Ostwald color wheel,
    when a hue closest to the pre-urine-contact color is specified as a first hue and a hue closest to the post-urine-contact color is specified as a second hue, and
    when a hue closest to the pre-feces-contact color is specified as a third hue and a hue closest to the post-feces-contact color is specified as a fourth hue,
    a difference in color number between the third hue and the fourth hue is larger than a difference in color number between the first hue and the second hue in the Ostwald color wheel.

12. The absorbent article according to claim 1, wherein among the 24 color hues of the Ostwald color wheel,
    when a hue closest to the pre-urine-contact color is specified as a first hue and a hue closest to the post-urine-contact color is specified as a second hue, and
    when a hue closest to the pre-feces-contact color is specified as a third hue and a hue closest to the post-feces-contact color is specified as a fourth hue,
    a difference in color number between the first hue and the second hue is equal to a difference in color number between the third hue and the fourth hue in the Ostwald color wheel.

* * * * *